United States Patent
Weber et al.

(10) Patent No.: US 9,084,569 B2
(45) Date of Patent: *Jul. 21, 2015

(54) METHOD AND APPARATUS FOR REDUCING COUPLING BETWEEN SIGNALS IN A MEASUREMENT SYSTEM

(71) Applicant: CERCACOR LABORATORIES, INC., Irvine, CA (US)

(72) Inventors: Walter M. Weber, Laguna Hills, CA (US); Ammar Al-Ali, San Juan Capistrano, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/216,583

(22) Filed: Mar. 17, 2014

(65) Prior Publication Data

US 2014/0200422 A1    Jul. 17, 2014

Related U.S. Application Data

(63) Continuation of application No. 12/983,823, filed on Jan. 3, 2011, now Pat. No. 8,676,286, which is a continuation of application No. 11/371,242, filed on Jan. 23, 2006, now Pat. No. 7,865,222, which is a continuation of application No. 10/615,333, filed on Jul. 8, 2003, now Pat. No. 7,003,338.

(51) Int. Cl.
*A61B 5/1455* (2006.01)
*A61B 5/00* (2006.01)

(52) U.S. Cl.
CPC .......... *A61B 5/14552* (2013.01); *A61B 5/14551* (2013.01); *A61B 5/7203* (2013.01); *A61B 5/7228* (2013.01); *A61B 5/7221* (2013.01)

(58) Field of Classification Search
CPC ........... A61B 5/14551; A61B 5/14552; A61B 5/7203; A61B 5/7221; A61B 5/7228
USPC .................................. 600/310, 322, 323, 336
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |

(Continued)

*Primary Examiner* — Eric Winakur

(74) *Attorney, Agent, or Firm* — Knobbe Martens Olson & Bear LLP

(57) ABSTRACT

A method and an apparatus for separating a composite signal into a plurality of signals is described. A signal processor receives a composite signal and separates a composite signal in to separate output signals. Pre-demodulation signal values are used to adjust the demodulation scheme.

20 Claims, 4 Drawing Sheets

(56) References Cited

U.S. PATENT DOCUMENTS

| | | |
|---|---|---|
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,800,348 A | 9/1998 | Kaestle |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,921,921 A | 7/1999 | Potratz et al. |
| 5,934,925 A | 8/1999 | Tobler et al. |
| 5,940,182 A | 8/1999 | Lepper, Jr. et al. |
| 5,995,855 A | 11/1999 | Kiani et al. |
| 5,995,858 A | 11/1999 | Kinast |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,363,269 B1 | 3/2002 | Hanna et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,505,133 B1 | 1/2003 | Hanna et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |

(56) References Cited

U.S. PATENT DOCUMENTS

| | | |
|---|---|---|
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |

(56) References Cited

U.S. PATENT DOCUMENTS

| | | |
|---|---|---|
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 2001/0002206 A1 | 5/2001 | Diab et al. |

METHOD AND APPARATUS FOR REDUCING COUPLING BETWEEN SIGNALS IN A MEASUREMENT SYSTEM

REFERENCE TO RELATED APPLICATIONS

The present application is a continuation of U.S. application Ser. No. 12/983,823, filed Jan. 3, 2011, titled "Method and Apparatus for Reducing Coupling Between Signals in a Measurement System," which is a continuation of U.S. application Ser. No. 11/371,242, filed Jan. 23, 2006, titled "Method and Apparatus for Reducing Coupling Between Signals in a Measurement System," which is a continuation of U.S. application Ser. No. 10/615,333, filed Jul. 8, 2003, titled "Method and Apparatus for Reducing Coupling Between Signals," the entire contents of which is hereby incorporated by reference.

BACKGROUND

1. Field

The present disclosure relates to the field of signal processing, and, more particularly, relates to multi-channel demodulators for demodulating mixed signals, such as, for example, signals generated in a pulse oximetry system.

2. Description of the Related Art

In many multi-channel measurement and communication systems, crosstalk between channels and corruption of data within the channels are significant problems. Such problems can arise from variations in manufacturing tolerances, movement, propagation delays, phase shifts, temperature effects, degradation of components due to age or other factors, noise, etc.

A pulse oximetry system is one example of a system where the above-referenced problems are found. In a pulse oximetry system, blood oxygen saturation is determined by transmitting pulses of electromagnetic energy through a portion of a subject having blood flowing therein (e.g., through a finger, through an ear lobe, or other portion of the body where blood flows close to the skin). The pulses of electromagnetic energy comprise periodic pulses of red light having wavelengths of approximately 660 nanometers, for example, and periodic pulses of infrared light having wavelengths of approximately 905 nanometers.

After propagating through the portion of the subject, the red pulses and the infrared pulses are detected by a detector which is responsive to light at both wavelengths and which generates an electrical signal that has a relationship to the intensity of the electromagnetic energy incident on the detector. The detector output is a two-channel signal having a first signal component corresponding to the detected red pulses and a second signal component corresponding to the detected infrared pulses.

The two-channel signal is demodulated to recover separate signals corresponding to the first signal component and the second signal component. However, prior art demodulators are not sufficiently accurate enough to completely separate the two signal components in all cases. Thus, it is not uncommon for the first demodulator output signal (corresponding to the first signal component) to contain residual components of the second signal and vice versa. This crosstalk between the first and second signal components reduces the accuracy of the recovered first and second signals. In multi-channel systems with more than two channels, crosstalk can occur between all of the channels, again reducing accuracy.

SUMMARY

The present disclosure solves these and other problems by separating a combined multi-channel signal into a plurality of output signals in a manner that reduces crosstalk and other contamination in the plurality of output signals. In one embodiment, the separator includes a multi-channel demodulator that is first configured using nominal values for the various components in the signal path. In one embodiment, the multi-channel demodulator is further configured using data obtained from calibration measurements. In one embodiment, the calibration measurements are made during an initialization period. In one embodiment, the calibration measurements are made frequently, continuously, or at selected intervals. In one embodiment, calibrations are performed on at least one of, initialization, on command, on attachment of a new sensor, continuously, and/or interspersed with measurements. In one embodiment of a system for measuring one or more blood constituents, the calibration measurements are made when the system detects that a patient has been connected to the system. In one embodiment, the multi-channel demodulator is further configured at regular intervals by re-running the calibration measurements. In one embodiment, the multi-channel demodulator comprises an optimizing demodulator. In one embodiment, crosstalk in the multi-channel demodulator is reduced by computing an amplitude and/or phase adjustment of one or more demodulation signals that are provided respectively to one or more mixers.

In one embodiment, an apparatus for measuring blood oxygenation in a subject includes a first signal source which applies a first input signal during a first time interval. A second signal source applies a second input signal during a second time interval. A detector detects a first parametric signal responsive to the first input signal passing through a portion of the subject having blood therein and detects a second parametric signal responsive to the second input signal passing through the portion of the subject. The detector generates a detector output signal responsive to the first and second parametric signals. A signal processor receives the detector output signal and demodulates the detector output signal by applying a first demodulation signal to a signal responsive to the detector output signal to generate a first demodulator output signal and applying a second demodulation signal to the signal responsive to the detector output signal to generate a second demodulator output signal. In one embodiment, the first demodulation signal has at least one component comprising a first frequency, a first phase, and a first amplitude; and the second demodulation signal has at least one component comprising a second frequency, a second phase, and a second amplitude. In one embodiment, the first phase and the second phase are chosen to reduce crosstalk from the first parametric signal to the second demodulator output signal and to reduce crosstalk from the second parametric signal to the first demodulator output signal. In one embodiment, the first amplitude and the second amplitude are chosen to reduce crosstalk from the first parametric signal to the second demodulator output signal and to reduce crosstalk from the second parametric signal to the first demodulator output signal. In one embodiment, at least one of the first amplitude, the first phase, the second amplitude, and the second phase are chosen to reduce crosstalk from the first parametric signal to the second demodulator output signal and to reduce crosstalk from the second parametric signal to the first demodulator output signal.

In one embodiment, at least one of the first amplitude, the first phase, the second amplitude, and the second phase is determined by turning off one of the first and second signal sources and measuring the crosstalk between one of the parametric signals and the non-corresponding output signal.

One embodiment includes a method of reducing crosstalk between two signals generated by applying a first pulse and a second pulse to measure a parameter. The first pulse and the second pulse are applied periodically at a repetition rate defining a period. The first pulse is generated during a first interval in each period and the second pulse is generated during a second interval in each period. In one embodiment, the second interval is spaced apart from the first interval. In one embodiment, the second interval overlaps at least a portion of the first interval. The first and second pulses produce first and second parametric signals responsive to the parameter. The first and second parametric signals are received by a detector which outputs a composite signal responsive to the first and second parametric signals. The method includes applying a first demodulation signal to the composite signal to generate a first demodulated output signal. The first demodulation signal includes at least one component having at least a first amplitude and a first phase. The method further includes applying a second demodulation signal to the composite signal to generate a second demodulated output signal. The second demodulation signal includes at least one component having at least a second amplitude and a second phase. The method further includes lowpass filtering the first demodulated output signal to generate a first recovered output signal responsive to the first parametric signal, and lowpass filtering the second demodulated output signal to generate a second recovered output signal responsive to the second parametric signal. The method also includes choosing at least one of the first phase, the first amplitude, the second phase, and the second amplitude to reduce crosstalk components in the first recovered output signal and the second recovered output signal. In one embodiment, the method also includes choosing the first phase and/or the second phase to reduce crosstalk components in the first recovered output signal and the second recovered output signal.

In one embodiment, the first phase and the second phase are chosen by applying a first light pulse pattern during a first time period and measuring the first recovered output during the first time period as a first calibration output, and measuring the second recovered output during the first time period as a second calibration output. The method includes applying a second light pulse pattern during a second time period and measuring the first recovered output during the first time period as a third calibration output and measuring the second recovered output during the second time period as a fourth calibration output. The method further includes computing the first phase and the second phase from at least the first calibration output, the second calibration output, the third calibration output, and the fourth calibration output.

In one embodiment the first phase is computed from a ratio of the first calibration output and the second calibration output.

In one embodiment, the first demodulation signal includes a sum of a first demodulation component having a first amplitude and a second demodulation component having a second amplitude. The second demodulation component is in quadrature with the first demodulation component and the act of choosing the first phase involves choosing the first amplitude and the second amplitude. In one embodiment the quadrature components are sinusoidal and cosinusoidal.

In one embodiment, the first demodulation signal includes a sum of a sinusoidal component having a first amplitude and a cosinusoidal component having a second amplitude. The first amplitude and the second amplitude are chosen by a least squares minimization of an error corresponding to the crosstalk. In one embodiment, the error is integrated over a time period corresponding to an integer number of cycles of the sinusoidal component.

In one embodiment, a first demodulation signal is applied to a composite signal having first and second coefficients to generate a first demodulated signal. The first demodulation signal includes a first component having a first amplitude and a second component having a second amplitude. The first and second components being in quadrature. The second amplitude has a predetermined relationship to the first amplitude. The predetermined relationship is selected to cause the first demodulated signal to have lower frequency components that include a primary component corresponding primarily to the first desired component and a residual component corresponding to the second component. The first demodulated signal is lowpass filtered to generate a first output signal. At least one of the first amplitude and the second amplitude are adjusted to reduce the residual component with respect to the primary component.

In one embodiment, a pulse oximetry system includes a modulation signal generator. The modulation signal generator generates a first modulation signal including a first pulse at a repetition frequency having a first duty cycle. The modulation signal generator generates a second modulation signal including a second pulse which also repeats at the repetition frequency and having a second duty cycle. The second pulse can be non-overlapping with respect to the first pulse, or the second pulse can partially or completely overlap the first pulse. The first and second pulses include a plurality of components wherein a first component has a frequency corresponding to the repetition frequency and a second component has a second frequency corresponding to twice the first frequency. A first transmitter emits electromagnetic energy at a first wavelength in response to the first pulse. A second transmitter emits electromagnetic energy at a second wavelength in response to the second pulse. A detector receives electromagnetic energy at the first and second wavelengths after passing through a portion of a subject. The detector generates a detector output signal responsive to the received electromagnetic energy. The detector output signal includes a signal component responsive to attenuation of the electromagnetic energy at the first wavelength and a signal component responsive to attenuation of the electromagnetic energy at the second wavelength. A first demodulator multiplies the detector signal by a first demodulation signal and generates a first demodulated output signal. A second demodulator multiplies the detector signal by a second demodulation signal and generates a second demodulated output signal. A configuration module configures the first demodulation signal and the second demodulation signal to substantially separate the first demodulator output and the second demodulator output.

In one embodiment, the configuration module selects a phase relationship between the first demodulation signal and the second demodulation signal.

In one embodiment, the configuration module configures the first demodulation signal and the second demodulation signal using, at least in part, data obtained during a calibration period. In one embodiment, the calibration data includes first and second calibration data corresponding to the first and second demodulated output signals during a first time period, and third and fourth calibration data corresponding to the first and second demodulated output signals during a second time period. In one embodiment, the second transmitter is turned off during the first time period, and the first transmitter is turned off during the second time period.

In one embodiment, the configuration module configures the first demodulation signal and the second demodulation signal by adjusting initial parameters that define the first demodulation signal and the second demodulation signal.

The configuration module adjusts the initial parameters using, at least in part, the calibration data obtained during a calibration period.

BRIEF DESCRIPTION OF THE DRAWINGS

The present disclosure will be described below in connection with the accompanying figures.

DETAILED DESCRIPTION OF THE PREFERRED EMBODIMENT

Figure 1:
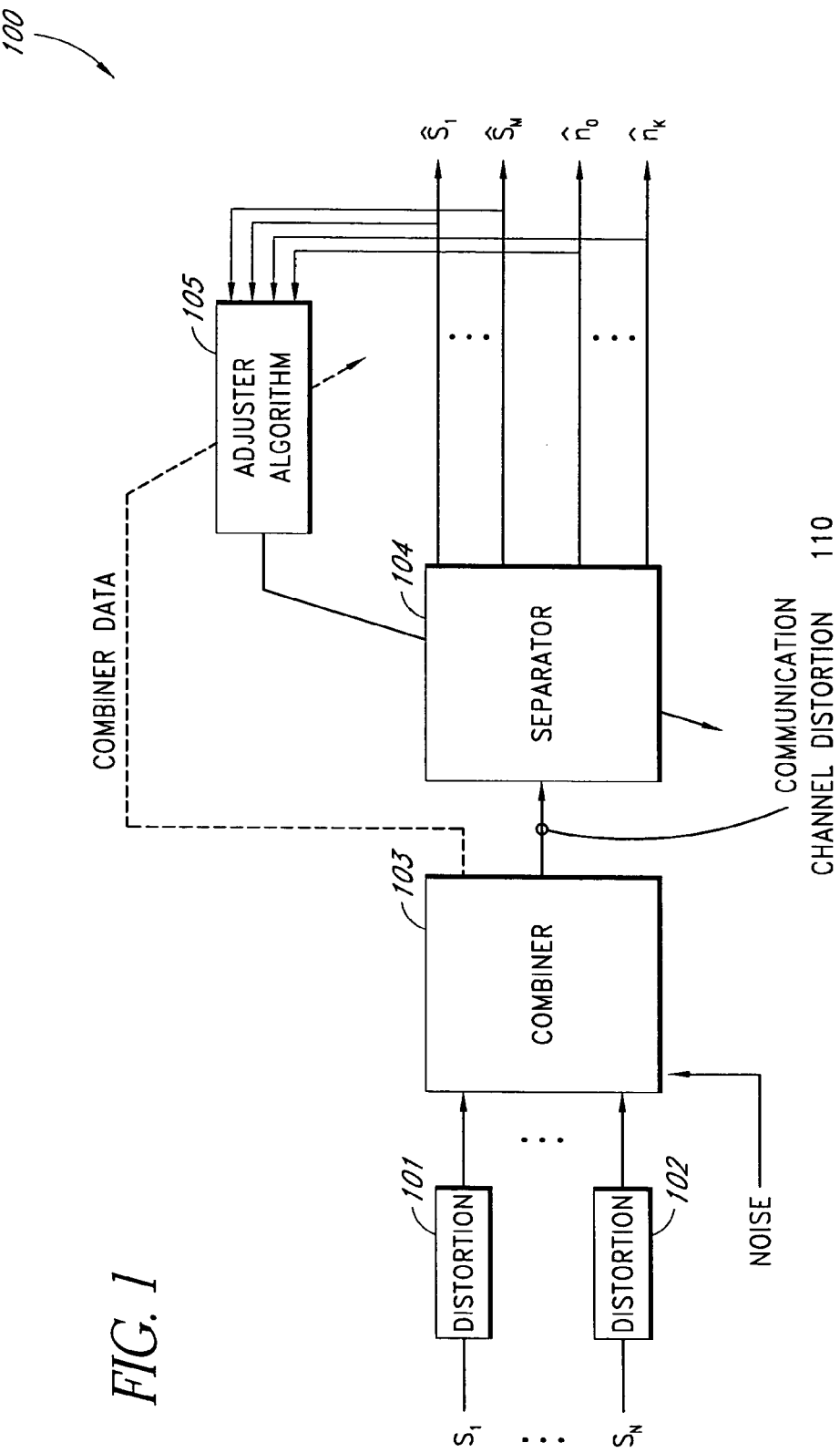
FIG. 1 is a block diagram of a multi-channel processing system that uses feedback from one or more outputs to configure the operation of a signal separator that separates a composite signal into a plurality of output signals.

FIG. 1 shows a topology of a multi-channel measurement or communication system 100. The system 100 has a signal combiner 103 for combining one or more input signals $S_1 \ldots S_N$ into a composite signal and a signal separator 104 for separating the composite signal into one or more output signals $\hat{S}_1 \ldots \hat{S}_M$. The output signals $\hat{S}_1 \ldots \hat{S}_M$ can include estimates of the input signals $S_1 \ldots S_N$. The input signals $S_1 \ldots S_N$ are corrupted by pre-combination distortion 101-102 respectively, and, optionally, by combination distortion in the signal combiner 103. The combiner 103 combines the N input signals into a composite signal (or composite signals). The combiner 401 can combine signals by addition, subtraction, multiplication, division, modulation, non-linear processes, linear processes, estimation, combinations thereof, etc. The composite signal is provided through a communication channel to the separator 104. The composite signal is distorted by communication channel distortion 110. The separator 104 separates the composite signal into M output signals, where M can be less than N, greater than N, or equal to N. In one embodiment, the separator also provides one or more additional output signals $\hat{n}_0 \ldots \hat{n}_K$ corresponding to estimates of other signals, such as, for example, noise signals, error signals, etc.

Due to errors in the system 100, the output signals $\hat{S}_1 \ldots \hat{S}_M$ are typically not exact copies of the input signals, but rather are estimates of the input signals. The accuracy of these estimates is a measure of system performance. The pre-combination distortion 101-102, the combiner distortion, and/or the channel distortion 110 tend to introduce crosstalk between the channels and thereby corrupt the output signals. The pre-combination distortion 101-102, combiner distortion, and the channel distortion 110 can be caused by variations in manufacturing tolerances, delay, movement, temperature effects, degradation of components due to age or other factors, noise, etc.

A module 105 is provided to configure the separator 104 to improve the quality of the separation function and thereby improve the quality of the output signals. One or more of the output signals from the separator are provided to the module 105 to provide feedback regarding the quality of the output signals and/or feedback regarding the operation of the separator 104. The module 105 uses feedback from one or more of the output signals $\hat{S}_1 \ldots \hat{S}_M$ (and, optionally, the output signals $\hat{n}_0 \ldots \hat{n}_K$) to monitor the quality of the separation function and to provide control information to control the operation of the separator. In one embodiment, the module 105 is configured by using configuration data obtained from the combiner 103. Such configuration data can be obtained by calibration procedures that test the operation of the combiner 103 before or during system use.

In one embodiment, the module 105 configures demodulators in the signal separator 104 using, at least in part, calibration data obtained during a calibration period. For example, in one embodiment involving a two channel system, the calibration data includes first and second calibration data corresponding to the first and second output signals during a first time period, and third and fourth calibration data corresponding to the first and second demodulated output signals during a second time period. In one embodiment, the second transmitter is turned off during the first time period, and the first transmitter is turned off during the second time period. In one embodiment, the module 105 configures the first demodulation signal and the second demodulation signal by adjusting initial parameters that define the first demodulation signal and the second demodulation signal. The configuration module adjusts the initial parameters using, at least in part, the calibration data obtained during a calibration period.

Figure 2:
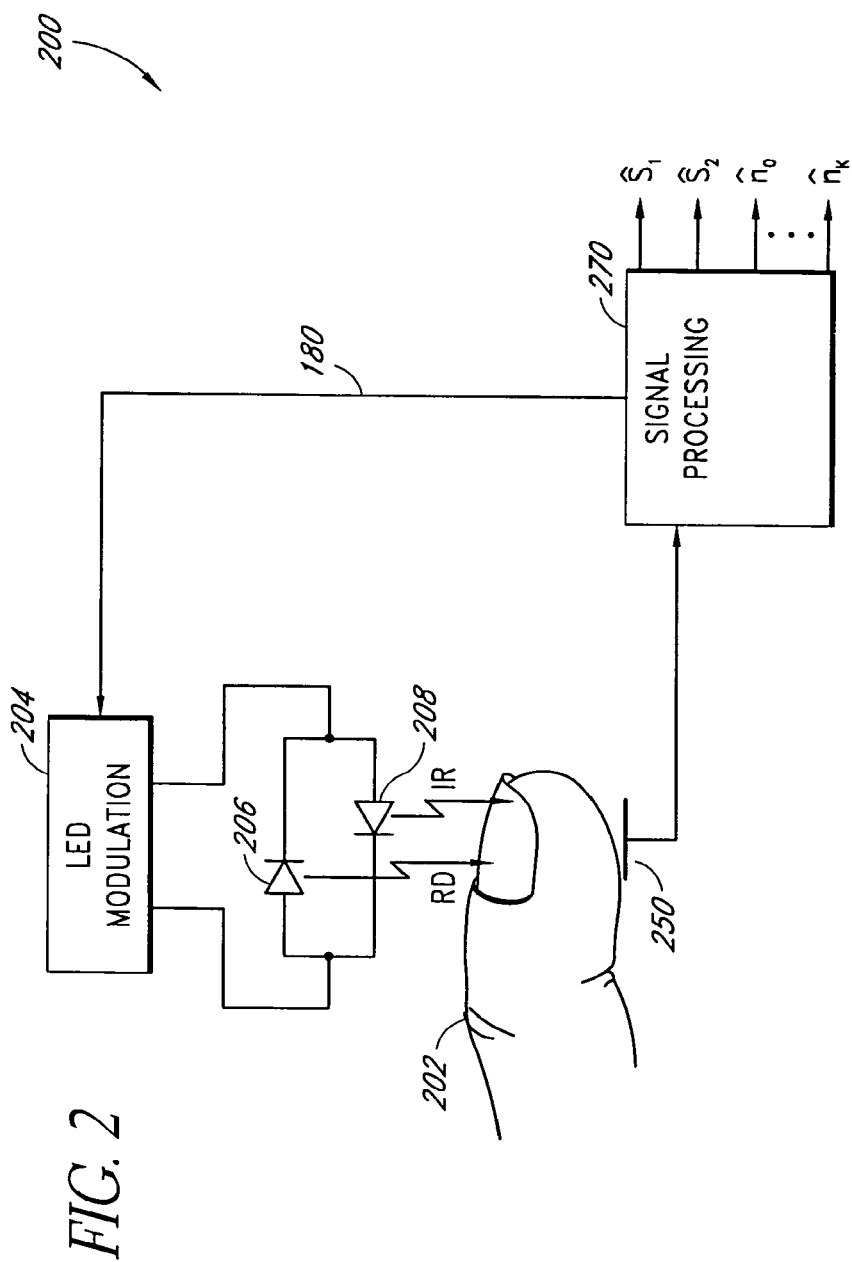
FIG. 2 is a block diagram of a two-channel signal processing system to determine blood oxygen saturation in a subject, wherein illumination is provided by back-to-back Light-Emitting Diodes (LEDs).

FIG. 2 is a block diagram of a two-channel signal processing system 200 that fits the general topology shown in FIG. 1. The system 200 is configured to determine one or more blood constituents in a subject, such as, for example, a human subject. In the example presented, the measurements are performed on a portion of the subject, such as a finger 202 illustrated in FIG. 2A. An LED modulation circuit 204 drives a pair of back-to-back light emitting diodes (LEDs) 206, 208 by applying a periodic signal to the two light emitting diodes 206, 208. Light from the diodes 206, 208 passes through the finger 202 and is detected by a detector 250. An output from the detector 250 is provided to a signal processing block 270. A control output from the signal processing block 270 is provided to the LED modulation circuit 204. The signal processing block 270 also provides outputs $\hat{S}_1$ and $\hat{S}_2$ corresponding to the light detected from the diodes 206, 208, and, optionally, output signals $\hat{n}_0 \ldots \hat{n}_K$ corresponding to estimates of noise or other signals.

In one embodiment, the LED 206 is selected to emit electromagnetic energy in the red visible light range, and has a wavelength of, for example, approximately 660 nanometers. The LED 208 is selected to emit electromagnetic energy in the infrared range, and has a wavelength of, for example, approximately 905 nanometers. The LED modulation circuit 204 supplies current to activate the LEDs 206 and 208. Each LED is activated for a time period $\tau$ which can be different for the different LEDs. The pulses from the LEDs 206 and 208 repeat with a periodicity T.

Figure 3:
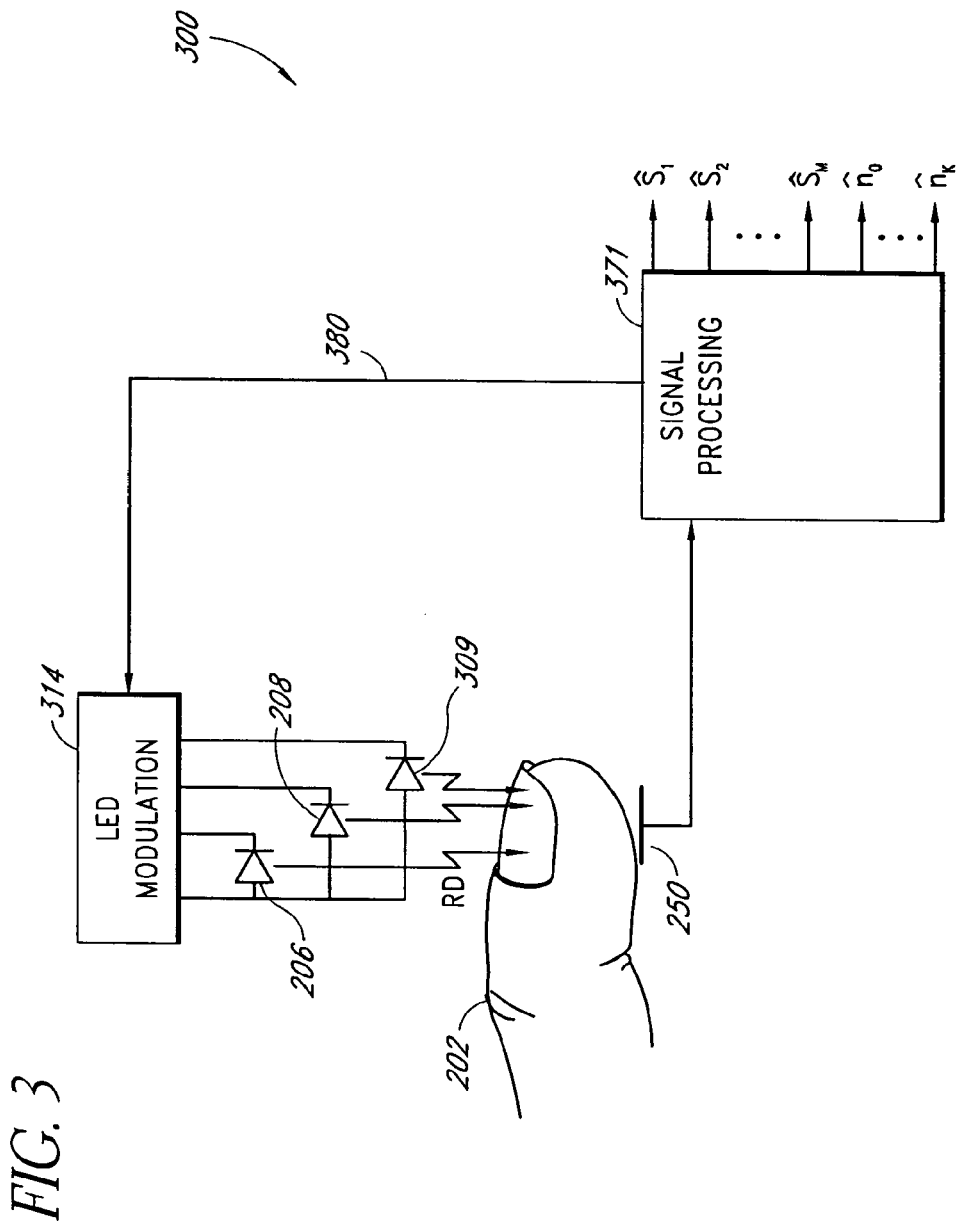
FIG. 3 is a block diagram of a multi-channel signal processing system to determine blood constituents (e.g., oxygen saturation) in a subject, wherein illumination is provided by N diodes or illumination sources.

FIG. 3 is a block diagram of a multi-channel signal processing system 300 that also fits the topology shown in FIG. 1. Like the system 200, the system 300 is configured to determine blood oxygen saturation or other blood constituents in a subject, such as, for example, a human subject. In FIG. 3, an LED modulation circuit 314 drives N diodes, where N is two or greater, thus allowing greater flexibility than the system 200. In FIG. 3, the diodes 206 and 208 are shown, along with an N'th diode 309, it being understood that the diode 309 is omitted if N=2. The LED modulation circuit 314 is configured to allow the diodes 206, 208, and 309 to be driven independently such that the diodes can be driven at separate times or in overlapping time periods if desired. Light from the diodes 206, 208, 309 passes through the finger 202 and is detected by the detector 250. The output from the detector 250 is provided to a signal processing block 371. A control output from the signal processing block 371 is provided to the LED modulation circuit 314. The signal processing block 371 also provides outputs $S_1$ through $S_M$, where M is greater than or equal to one, but need not be equal to N.

Figure 4:
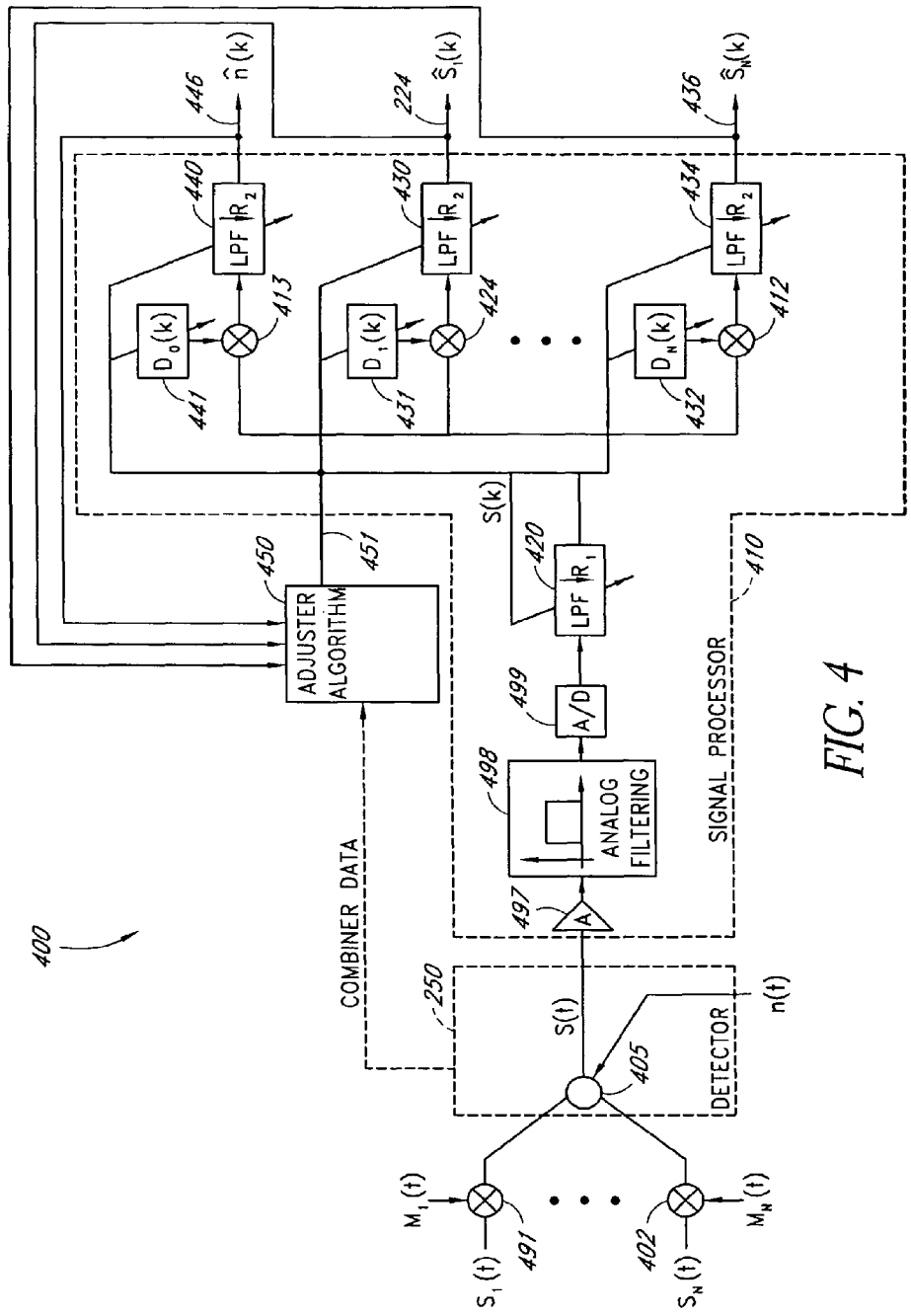
FIG. 4 is a block diagram of a specific embodiment of the multi-channel processing system of FIG. 1.

FIG. 4 shows one embodiment of an adjustable multi-channel modulator/demodulator system 400. The system 400 is based on the topology of the system 100 and can be used in a system for measuring blood constituents (e.g., pulse oximetry, carboxyhemoglobin, etc.) as shown in FIGS. 2 and 3. In the system 400, an input $S_1(t)$ and a modulation input $M_1(t)$ are provided to a first modulator 491. A signal input $S_N(t)$ and a modulation input $M_N(t)$ are provided to an $N^{th}$ modulator 402.

The photodetector 250 is modeled as an adder 405. The outputs of the modulators 491 and 402 are added together in the adder 405, in the presence of noise n(t) to generate a composite signal M(t) where:

$$S(t)=S_1(t)M_1(t)+ \ldots +S_N(t)M_N(t)+n(t) \quad (1)$$

The S(t) signal output of the adder 405 (i.e., the output of the detector 250) is applied to the input of a signal-processing block 410. Within the signal-processing block 410, the signal S(t) is passed through an amplifier 497 and through an analog bandpass filter 498. The analog bandpass filter 498 provides anti-aliasing and removal of low frequency noise and DC. The desired signal components in the signals $S_i(t)$ are frequency shifted by the operation of the modulation signals $M_i(t)$ and are passed by the analog bandpass filter 498.

The output of the analog bandpass filter 498 is sampled by an analog-to-digital converter 499 and converted therein to digital signals and provided to an input of an optional decimation block 420.

The filtered (and, optionally, decimated) signal S(t) is sampled to produce a sampled-data signal S(k) that is provided to the first input of the first mixer 424, to the first input of the N'th mixer 412, and to the first input of a noise channel mixer 413. A first demodulating signal $D_1(k)$ is provided to a second input of a first mixer 424 from a signal generator 431. The $N^{th}$ demodulating signal $D_N(k)$ is provided to an $N^{th}$ mixer 412 from an output of a signal generator 432. The noise demodulating signal $D_0(k)$ is provided to the noise channel mixer 413 from an output of a signal generator 441. A control input to each of the signal generators 431, 432, and 441 is provided by the output of the adjuster algorithm 450. In yet another embodiment, the adjuster algorithm 450 may also be controlled by other signal processing elements downstream of the signal processor 400.

The outputs of the mixers 413, 424, and 412 are provided as respective inputs to decimation blocks 440, 430, and 434 respectively. Each of the decimation blocks 440, 430, and 434 has a control input provided by the output of the adjuster algorithm block 450. The output of the decimation block 440 is an estimate of the signal n(t) and it is provided to an input of the adjuster algorithm block 450. In an alternate embodiment, the signal estimates $\hat{S}_i(k)$ are also provided to the adjuster algorithm block 450.

An output of the decimator 430 is a signal $\hat{S}_1(k)$, which, as discussed above, is an estimate of the signal $S_1(k)$ (where $S_1(k)$ corresponds to a sampled-data representation of $S_1(t)$). Likewise, the output of the decimation block 434 is an estimate of the signal $S_N(t)$. As shown above, the selection of the demodulating signals $D_i(t)$ for $i=0 \ldots N$ in accordance with the present disclosure substantially reduces or eliminates the effects of noise in the output signals $\hat{S}_i(k)$ and n(k), and also substantially reduces or eliminates crosstalk between the signals.

When the system 400 is used in connection with a blood constituent measurement system as shown in FIGS. 2 and 3 the red LED 206 provides a light intensity represented as $I_{RD}$, and the infrared LED 208 provides a light intensity represented as $I_{IR}$. The effects of turning the LEDs 206, 208 on and off on a periodic bases are modeled by the first multiplier or modulator 290 which applies a first modulation signal $M_1(t)$ to the red light intensity to generate a modulated red signal $I_{RDMOD}(t)$ and by a second multiplier the modulator 292 which applies a second modulation signal $M_2(t)$ to the infrared light intensity to generate a modulated infrared signal $I_{IRMOD}(t)$. The modulated light red signal and the modulated infrared signal are applied to the finger 202, or other body portion, as described above. The blood in the finger 202 has a volume and scattering components, which vary throughout each cardiac cycle. The blood carries oxygen and other materials therein. The oxygen content is a function of both the blood volume and the concentration of the oxygen in the blood volume. The concentration of the oxygen in the blood volume is generally measured as blood oxygen saturation for reasons which are described in full in U.S. Pat. Nos. 5,482,036 and 5,490,505, both of which are hereby incorporated by reference in their entirety. As further described in the two referenced patents, the blood oxygen saturation is determined by comparing the relative absorption of the red light and the infrared light in the finger 202. The comparison is complicated by the noise caused by movement, ambient light, light scattering, and other factors. The signals $S_1(t)$ and $S_2(t)$ represent the effect of the time-varying volume and scattering components of the blood in the finger 202 on the red light and the infrared light, respectively, passing through the finger 202 from the LEDs 206, 208 to the detector 250.

As shown in FIG. 4, a set of N+1 signals $S_i[k]i=1 \ldots N$, and n(k) are sampled at a desired sample rate. The signals are combined according to the formula:

$$S(k)=M_1(k)S_1(k)+ \ldots +M_N(k)S_N(k)+n(k) \quad (2)$$

In one embodiment, each of the decimators 420, 440, 430, and 434 includes a digital lowpass filter and a sample rate compressor. In one embodiment, the characteristics of the digital lowpass filters (e.g., the number of filter coefficients and values of the filter coefficients) and the sample rate compression factor of each decimator are fixed. In one embodiment, the characteristics of the digital lowpass filters (e.g., the number of filter coefficients or values of the filter coefficients) and the sample rate compression factor of each decimator are provided by the adjustment algorithm 450. The signal generators 431, 432 and 441 generate the demodulation sequences for the demodulators 424, 412, and 413 respectively. The demodulation sequences produced by the signal generators 431, 432 and 441 are controlled by the adjuster algorithm 450.

In one embodiment, the adjuster algorithm 450 adjusts the pre-demodulation decimation rate $R_1$ (in the demodulator 420), and the post-demodulation decimation rate $R_2$ (in the demodulators 430, 434 and 440) according to the noise in the noise estimate $\hat{n}(k)$ and (optionally) according to the signals $\hat{S}_i(k)$. The product $R_1R_2$ is the total decimation rate from the signal S(k) at the output of the A/D converter 499 to the signals $\hat{S}_i(k)$ at the output of the signal processing block 400. The adjuster algorithm may adjust $R_1$ and $R_2$ such that the product $R_1R_2$ varies, or the adjuster algorithm may adjust $R_1$ and $R_2$ such that the product $R_1R_2$ is substantially constant. Typically, the adjuster algorithm will keep the $R_1R_2$ product constant so that the signal processing blocks downstream of the signal processor 400 will operate at a substantially constant sample rate.

In one embodiment, the adjuster algorithm 450 adjusts the demodulation signals $D_i(k)$ to reduce or eliminate crosstalk. In one embodiment, the adjuster algorithm 450 reduces crosstalk by configuring the demodulators, as discussed in more detail below.

One skilled in the art will recognize that the lowpass filters provided in connection with the decimation blocks can provide other filter functions in addition to lowpass filtering. Thus, for example, the lowpass filters 420, 430, 440, and 450, and the decimators 420, 430, 434, and 440 can provide other filter functions (in addition to lowpass filtering) such as, for example, bandpass filtering, bandstop filtering, etc. Moreover, the post-demodulation decimation rate $R_2$ need not be the same for each output channel. Thus, for example, in FIG. 4, the decimator 440 can have a first decimation rate $R_2=r_1$ while the decimators 430 and 434 have a second decimation rate $R_2=r_2$.

The demodulators above are described in terms of digital signal processing on sampled data. Thus, the demodulator signals are written $D_i(k)$. The demodulators and the filtering associated with the demodulators can be done in using analog processing (using time-domain demodulator signals $D_i(t)$) or on sampled data signals (using digital-domain demodulator signals $D_i(k)$). For convenience, the following development describes the demodulator signals primarily in the time domain, with the understanding that the modulators can be implemented using digital signal processing or analog processing.

The characteristics of the demodulation signals $D_1(t)$ and $D_2(t)$ affect how much crosstalk is seen in the output signals. In an diagonal system, that is, when the demodulator has been diagonalized, there is, ideally, no crosstalk. The first output signal $\hat{S}_1(t)$ is an estimate (or approximation) to the signal $S_1(t)$. Similarly, the second output signal $\hat{S}_2(t)$ is an estimate (or approximation) to the signal $S_2(t)$. When the composite signal $S(t)$ is a linear combination of the signals $S_i(t)$, then the relationship between the signals $S_i(t)$ and the signals $\hat{S}_i(t)$. When $M_1=\cos \omega t$, $M_2=\sin \omega t$, $n(t)=0$, and there is no distortion (e.g., no pre-combination, combiner, or channel distortion) then:

$$S(t)=S_1(t)\cos \omega t + S_2(t)\sin \omega t \qquad (3)$$

Then:

$$\hat{S}_1(t)=LP[D_1(t)S(t)] \qquad (4)$$

$$\hat{S}_2(t)=LP[D_2(t)S(t)] \qquad (5)$$

If:

$$D_1(t)=2\cos \omega t \qquad (6)$$

$$D_2(t)=2\sin \omega t \qquad (7)$$

then $$D_1(t)S(t) = 2S_1(t)\cos^2 \omega t + 2S_2(t)\sin\omega t \cos\omega t \qquad (8)$$
$$= S_1(t) - S_1(t)\cos 2\omega t + S_2(t)\sin 2\omega t$$

After lowpass filtering to remove the terms with a frequency of $2\omega t$ and higher $$\hat{S}_1(t)=S_1(t) \qquad (9)$$

Similarly for $$\hat{S}_2(t)=LP[D_2(t)S(t)] \qquad (10)$$

then $$D_2(t)S(t) = 2S_1(t)\sin\omega t \cos\omega t + 2S_2(t)\sin^2\omega t \qquad (11)$$
$$= S_2(t) - S_2(t)\cos 2\omega t + S_1(t)\sin 2\omega t$$

After lowpass filtering to remove the terms with a frequency of $2\omega t$ $$\hat{S}_2(t)=S_2(t) \qquad (12)$$

In the above analysis, it was assumed that there are no time delays or phase shifts in the signal $S(t)$, and thus, configuration is relatively straightforward When an unknown delay (or phase error) is introduced, then the signals are no longer diagonal. Consider, for example, the situation when a delay $\Delta$ is introduced into the composite signal. Then:

$$S(t)=\cos \omega(t-\Delta)S_1(t-\Delta)+\sin \omega(t-\Delta)S_2(t-\Delta)$$

It then follows that:

$$\hat{S}_1(t) = LP[2\cos\omega t(\cos\omega(t-\Delta)S_1(t-\Delta) + \sin\omega(t-\Delta)S_2(t-\Delta))]$$
$$= LP[2\cos\omega t(\cos\omega t\cos\omega\Delta + \sin\omega t\sin\omega\Delta)S_1(t-\Delta)] +$$
$$LP[2\cos\omega t(\sin\omega t\cos\omega\Delta - \cos\omega t\sin\omega\Delta)S_2(t-\Delta)]$$
$$= \cos\omega\Delta S_1(t-\Delta) - \sin\omega\Delta S_2(t-\Delta)$$

The above equations can be expressed in matrix form as:

$$\begin{bmatrix} \hat{S}_1(t) \\ \hat{S}_2(t) \end{bmatrix} = \begin{bmatrix} \cos\omega\Delta & -\sin\omega\Delta \\ \sin\omega\Delta & \cos\omega\Delta \end{bmatrix} \begin{bmatrix} S_1(t-\Delta) \\ S_2(t-\Delta) \end{bmatrix} \qquad (13)$$

Then $$\begin{bmatrix} S_1(t-\Delta) \\ S_2(t-\Delta) \end{bmatrix} = \begin{bmatrix} \cos\omega\Delta & \sin\omega\Delta \\ -\sin\omega\Delta & \cos\omega\Delta \end{bmatrix} \begin{bmatrix} \hat{S}_1(t) \\ \hat{S}_2(t) \end{bmatrix} \qquad (14)$$

The above equation can be expressed as $$\begin{bmatrix} S_1(t-\Delta) \\ S_2(t-\Delta) \end{bmatrix} = \begin{bmatrix} \cos\omega\Delta & \sin\omega\Delta \\ -\sin\omega\Delta & \cos\omega\Delta \end{bmatrix} \cdot LP\begin{bmatrix} D_1(t)S(t) \\ D_2(t)S(t) \end{bmatrix} \qquad (15)$$
$$= LP\left[\begin{bmatrix} \cos\omega\Delta & \sin\omega\Delta \\ -\sin\omega\Delta & \cos\omega\Delta \end{bmatrix} \begin{bmatrix} D_1(t) \\ D_2(t) \end{bmatrix} S(t)\right]$$
$$= LP\left[\begin{bmatrix} \overline{D}_1(t) \\ \overline{D}_2(t) \end{bmatrix} S(t)\right]$$

where $$\overline{D}_1(t) = \cos\omega\Delta D_1(t) + \sin\omega\Delta D_2(t)$$
$$= 2\cos\omega\Delta\cos\omega t + 2\sin\omega\Delta\sin\omega t$$

and similarly for $\overline{D}_2(t)$. Thus the modified demodulation functions $\overline{D}_1(t)$ and $\overline{D}_2(t)$ can be expressed as a linear combination of basis functions. If the time delay $\Delta$ can be predicted, then the demodulator functions can be calculated and programmed into the communication system. However, in many cases the time delay Δ is not known or changes over time. As described below, the demodulator functions can be determined by system calibration procedures.

When an unknown phase shift (or phase error) is introduced, then there may be crosstalk in the system. Consider, for example, the situation when a phase error $\phi_1$ occurs in the signal $S_1(t)$ and a phase error $\phi_2$ occurs in the signal $S_2(t)$. The phase errors can be caused by intrinsic properties of the components, intrinsic properties of the system, component variations, time delays, etc. In the presence of the phase errors:

$$D_1(t)S(t) = 2A_1 S_1(t)\sin(\omega t + \phi_1)\sin\omega t + \qquad (16)$$
$$2A_2 S_2(t)\cos(\omega t + \phi_2)\sin\omega t$$
$$= 2A_1 S_1(t)\sin\omega t[\sin\omega t\cos\phi_1 + \cos\omega t\sin\phi_1] +$$
$$2A_2 S_2(t)\sin\omega t[\cos\omega t\cos\phi_2 + \sin\omega t\sin\phi_2]$$
$$= A_1 S_1(t)\cos\phi_1 - A_1 S_1(t)\cos\phi_1 2\omega t +$$
$$A_1 S_1(t)\sin\phi_1 \sin 2\omega t + A_2 S_2(t)\cos\phi_2 \sin\omega t -$$
$$A_2 S_2(t)\sin\phi_2 + A_2 S_2(t)\sin\phi_2 \cos 2\omega t$$

Thus, after lowpass filtering $$\hat{S}_1(t) = A_1 S_1(t)\cos\phi_1 - A_2 S_2(t)\sin\phi_2 \qquad (17)$$

The above equation shows crosstalk because $\hat{S}_1(t)$ depends in part on components of $S_2(t)$ when $A_2 \neq 0$ and $\phi_2 \neq n\pi$ where $n=0, \pm1, \pm2 \ldots$.

Similarly, $$\hat{S}_1(t) = A_1 S_1(t)\sin\phi_1 - A_2 S_2(t)\cos\phi_2 \qquad (17)$$

The above equations can be expressed in matrix form as:

$$\begin{bmatrix} \hat{S}_1(t) \\ \hat{S}_2(t) \end{bmatrix} = \begin{bmatrix} A_1\cos\phi_1 & -A_2\sin\phi_2 \\ A_1\sin\phi_1 & A_2\cos\phi_2 \end{bmatrix} \begin{bmatrix} S_1(t) \\ S_2(t) \end{bmatrix} \qquad (19)$$

After inversion $$\begin{bmatrix} S_1(t) \\ S_2(t) \end{bmatrix} = \frac{1}{\cos(\phi_1 - \phi_2)} \begin{bmatrix} \frac{\cos\phi_2}{A_1} & \frac{\sin\phi_1}{A_1} \\ -\frac{\sin\phi_2}{A_2} & \frac{\cos\phi_1}{A_2} \end{bmatrix} \begin{bmatrix} \hat{S}_1(t) \\ \hat{S}_2(t) \end{bmatrix} \qquad (20)$$

$$\begin{bmatrix} S_1(t) \\ S_2(t) \end{bmatrix} = \frac{1}{\cos(\phi_1 - \phi_2)} \begin{bmatrix} \frac{\cos\phi_2}{A_1} & \frac{\sin\phi_1}{A_1} \\ -\frac{\sin\phi_2}{A_2} & \frac{\cos\phi_1}{A_2} \end{bmatrix} \begin{bmatrix} D_1(t) \\ D_2(t) \end{bmatrix} S(t) \qquad (21)$$

Then $$\begin{bmatrix} S_1(t) \\ S_2(t) \end{bmatrix} = \begin{bmatrix} \overline{D}_1(t) \\ \overline{D}_2(t) \end{bmatrix} S(t) \qquad (22)$$

Where $\overline{D}_i(t)$ are modified demodulation functions, given by:

$$\begin{bmatrix} \overline{D}_1(t) \\ \overline{D}_2(t) \end{bmatrix} = \frac{1}{\cos(\phi_1 - \phi_2)} \begin{bmatrix} \frac{\cos\phi_2 \sin\omega t + \sin\phi_1 \cos\omega t}{A_1} \\ \frac{-\sin\phi_2 \sin\omega t + \cos\phi_1 \cos\omega t}{A_2} \end{bmatrix} \qquad (23)$$

The modified demodulation functions have the form $$\overline{D}_i(t) = \sum_{j=1}^{N} \alpha_j \Phi_j(t) \qquad (24)$$

Choosing the coefficients $\alpha_j$ to eliminate crosstalk configures the modulator.

In one embodiment, the coefficients $\alpha_j$ can be fixed coefficients computed using known properties of the system. However, as system properties change over time, such fixed coefficients may lead to unacceptably high levels of crosstalk. Moreover, variations from device to device may cause the fixed coefficients to give unacceptably high levels of crosstalk.

Higher performance (that is, lower crosstalk) can be obtained by computing the coefficients as part of a system calibration or initialization procedure. Such calibration can be performed during system startup (e.g., when the system is turned on, or when the system begins processing data, etc.) and/or at regular intervals. In one embodiment, the adjuster algorithm 450 computes the coefficients $\alpha_j$ from the calibration data. In one embodiment, the coefficients $\alpha_j$ are chosen by making four calibration-type measurements to measure four parameters $\xi_{11}, \xi_{12}, \xi_{21},$ and $\xi_{22}$, where:

$$\xi_{11} = \hat{S}_1|_{S_1=A, S_2=0} = A\alpha_1 \cos\phi_1 \qquad (25)$$
$$\xi_{12} = \hat{S}_1|_{S_1=0, S_2=B} = -B\alpha_2 \sin\phi_2 \qquad (26)$$
$$\xi_{21} = \hat{S}_2|_{S_1=A, S_2=0} = A\alpha_1 \sin\phi_1 \qquad (27)$$
$$\xi_{22} = \hat{S}_2|_{S_1=0, S_2=B} = B\alpha_2 \cos\phi_1 \qquad (28)$$

where A and B are amplitudes. Then $$a_1 = \frac{\sqrt{\xi_{11}^2 + \xi_{21}^2}}{A} \qquad (29)$$

$$a_2 = \frac{\sqrt{\xi_{12}^2 + \xi_{22}^2}}{B} \qquad (30)$$

$$\tan\phi_1 = \frac{\xi_{21}}{\xi_{11}} \qquad (31)$$

$$\tan\phi_2 = -\frac{\xi_{12}}{\xi_{22}} \qquad (32)$$

From the above equations, it is evident that crosstalk depends only $\phi_1$ and $\phi_2$. Moreover, $\phi_1$ and $\phi_2$ can be chosen to eliminate crosstalk without knowing A or B. This is useful for systems such as pulse oximetry systems where absolute measurements of a channel are difficult or impractical, but where relative measurements (e.g., channel-to-channel measurements) are practical.

The demodulation signals $D_i(t)$ can be generated using the values of $\phi_1$ and $\phi_2$ from the above equations. Alternatively, the demodulation signals $D_i(t)$ can be generated from quadrature components as:

$$D_1(t) = b_{11} \sin\omega t + b_{12} \cos\omega t \qquad (33)$$

$$D_2(t) = b_{21} \sin\omega t + b_{22} \cos\omega t \qquad (34)$$

where the coefficients $b_{ij}$ are computed from $\phi_1$ and $\phi_2$.

In one embodiment, the demodulation functions are adapted from baseline coefficients, which are then improved through a calibration or initialization procedure to produce actual coefficients. The baseline coefficients are typically obtained from known properties of the system. The actual coefficients are usually relatively close in value to the baseline coefficients. This provides one way to assess the operational status of the system and to evaluate the calibration procedure. In one embodiment, if the actual coefficients are too different from the baseline parameters then it is assumed that the calibration procedure failed in some manner or that the equipment has failed in some manner, and appropriate measures can be taken (e.g., alert the operator, sound a warning, etc.)

To find the actual coefficients, the demodulation functions are initially given by:

$$D_1(t) = \alpha_{11} \sin \omega t + \alpha_{12} \cos \omega t \tag{35}$$

$$D_2(t) = \alpha_{21} \sin \omega t + \alpha_{22} \cos \omega t \tag{36}$$

Where the coefficients $\alpha_{ij}$ are the baseline coefficients determined from known or assumed properties of the signal S(t). For example, in one embodiment $\alpha_{ij} = \delta_{ij}$. In one embodiment, where initial estimates are available for $\phi_1$ and $\phi_2$, then the values of $\alpha_{ij}$ can be computed as discussed above.

The crosstalk reduction obtained using demodulation functions based on the coefficients $\alpha_{ij}$ can often be improved by computing new coefficients $\overline{\alpha}_{ij}$ and corresponding new demodulation functions $\overline{D}_i(t)$ where:

$$\overline{D}_1(t) = \overline{\alpha}_{11} \sin \omega t + \overline{\alpha}_{12} \cos \omega t \tag{37}$$

$$\overline{D}_2(t) = \overline{\alpha}_{21} \sin \omega t + \overline{\alpha}_{22} \cos \omega t \tag{38}$$

The process of finding the coefficients $\overline{\alpha}_{ij}$ begins by measuring two data sets, $x_1(t)$ and $x_2(t)$, as follows:

$$x_1(t) = S(t)|_{S_1 = A, S_2 = 0} \tag{39}$$

$$x_2(t) = S(t)|_{S_1 = 0, S_2 = B} \tag{40}$$

The data sets $x_1(t)$ and $x_2(t)$ are used to enforce the following constraint:

$$\int_0^{nT} x_i(T) \overline{D}_i(t) dt = 0 \tag{41}$$

where i=1, 2, n=1, 2, 3 . . . , and T is a time period corresponding to one complete modulation cycle. From the above constraint and the definitions of the demodulation functions, it follows that:

$$\overline{\alpha}_{11} \int_0^{nT} x_1(t) \sin \omega t \, dt + \overline{\alpha}_{12} \int_0^{nT} x_1(t) \cos \omega t \, dt = 0 \tag{42}$$

$$\overline{\alpha}_{21} \int_0^{nT} x_2(t) \sin \omega t \, dt + \overline{\alpha}_{22} \int_0^{nT} x_2(t) \cos \omega t \, dt = 0 \tag{43}$$

It is convenient to define $$\gamma_{11} = \int_0^{nT} x_1(t) \sin \omega t \, dt \tag{44}$$

$$\gamma_{12} = \int_0^{nT} x_1(t) \cos \omega t \, dt \tag{45}$$

$$\gamma_{21} = \int_0^{nT} x_2(t) \sin \omega t \, dt \tag{46}$$

$$\gamma_{22} = \int_0^{nT} x_2(t) \cos \omega t \, dt \tag{47}$$

and to define $$\beta_{ij} = \frac{\gamma_{ij}}{\left[\sum_k \gamma_{ik}^2\right]^{1/2}} \tag{48}$$

where $$\sum_k \beta_{ik}^2 = 1 \tag{49}$$

Then $$\overline{\alpha}_{11} \beta_{11} + \overline{\alpha}_{12} \beta_{12} = 0 \tag{50}$$

$$\overline{\alpha}_{21} \beta_{21} + \overline{\alpha}_{22} \beta_{22} = 0 \tag{51}$$

In one embodiment, to reduce crosstalk, it is desired to find the coefficients $\overline{\alpha}_{ij}$ closest (in the sense of minimizing some specified error, such as, for example, a least squared error) to the coefficients $\alpha_{ij}$ such that the above constraints are satisfied. One solution, obtained by minimizing the least squared error is:

$$\overline{\alpha}_{ij} = a_{ij} - \left(\sum_k \alpha_{ik} \beta_{ik}\right) \beta_{ij} \tag{52}$$

The term in parentheses can be described as the baseline crosstalk.

One of ordinary skill in the art will recognize that optimization methods other than least squares can be used. The solution methods for configuration are, for simplicity, described above in terms of a two-channel system. Using the above teachings, the extension to multi-channel systems is straightforward.

Although described above in connection with a particular embodiment of the present disclosure, it should be understood the description of the embodiment is illustrative of the disclosure and are not intended to be limiting. Although described above in connection with a pulse oximetry system wherein a parameter to be measured is the attenuation of red and infrared light passing through a portion of a subject's body, it should be understood that the method and apparatus described herein can also be used for other measurements where two or more signals are passed through a system to be analyzed. In particular, the present disclosure can be used to demodulate two combined parametric signals responsive to the system to be analyzed where the two parametric signals have a predetermined timing relationship between them, as described herein. The disclosure can be used in connection with various physiological parameter measurement systems, such as, for example, systems that measure blood constituents, blood oxygen carboxyhemoglobin, methemoglobin, glucose, etc. Various modifications and applications may occur to those skilled in the art without departing from the true spirit and scope of the invention as defined in the appended claims.

What is claimed is:

1. A system which measures one or more physiological characteristics of a living subject non-invasively by measuring pulsing light of two or more wavelengths after attenuation by body tissue, the system comprising:
   at least one emitter configured to emit light of at least two or more different wavelengths using a modulation scheme that cycles the at least two or more different wavelengths, the at least one emitter positioned to emit light in the direction of a living subject;
   at least one detector configured to detect the light of the at least two or more different wavelengths emitted from the at least one detector after the light has been attenuated by tissue of the living subject, the detector further configured to generate a detector signal representative of the emitted light;
   a demodulation system configured to demodulate the detector signal, the demodulation system configured to adjust the demodulation of the detector signal to reduce crosstalk based, at least in part, on detector configuration data.

2. The system of claim 1, the demodulation system is further configured to adjust the demodulation based on previously demodulated signal values.

3. The system of claim 1, wherein the demodulation is adjusted during an initial calibration period.

4. The system of claim 3, wherein the demodulation is adjusted during periodic calibration periods during measurement.

5. The system of claim 2, wherein the previously demodulated signal values comprises a plurality of demodulated signal values corresponding respectively to the at least two or more different wavelengths.

6. The system of claim 5, wherein each of the plurality of demodulated signal values is determined using a demodulation coefficient.

7. The system of claim 1, wherein the demodulation system comprises a plurality of demodulation coefficients used to demodulate the detector signal.

8. The system of claim 7, wherein at least one demodulation coefficient is used for each of the at least two or more different wavelengths.

9. The system of claim 1, wherein the demodulation has been diagonalized.

10. A method of demodulating a composite signal generated by applying at least first and second periodic pulses of electromagnetic energy to a system having a physiological parameter to be measured and by non-invasively receiving signals responsive to said electromagnetic energy after attenuation by body tissue of a living subject, said signals received as a composite signal having at least first and second components responsive to said at least first and second pulses respectively, said method comprising:
    receiving, at one or more signal processors, a composite signal responsive to electromagnetic energy of at least first and second periodic pulses of electromagnetic energy after attenuation by body tissue;
    applying, using the one or more signal processors, a first demodulation scheme to said composite signal to generate at least a first demodulated signal; and
    automatically adjusting, using the one or more signal processors, the first demodulation scheme based at least in part on detector configuration data.

11. The method of claim 10, wherein the adjustment reduces crosstalk.

12. The method of claim 10, further comprising applying a second demodulation scheme to said composite signal to generate a second demodulated signal and adjusting the second demodulation scheme based at least in part on the second demodulated signal.

13. The method of claim 12, wherein said signal processor is further configured to adjust at least one of the first and second demodulation schemes in the absence of at least one of the first and second periodic pulses of electromagnetic energy.

14. The method of claim 12, wherein said signal processor is further configured to adjust at least one of the first and second demodulation schemes based on the demodulated signals in order to further reduce crosstalk interspersed with measurements.

15. The method of claim 10, wherein said adjusting occurs continuously.

16. The method of claim 10, wherein said adjusting occurs interspersed with measurements.

17. A system for demodulating a composite signal generated by applying at least first and second periodic pulses of electromagnetic energy to a system having a physiological parameter to be measured and by non-invasively receiving signals responsive to said electromagnetic energy after attenuation by body tissue of a living subject, said signals received as a composite signal having at least first and second components responsive to said at least first and second pulses respectively, said system comprising:
    means for receiving, at one or more signal processors, a composite signal responsive to electromagnetic energy of at least first and second periodic pulses of electromagnetic energy after attenuation by body tissue;
    means for applying, using the one or more signal processors, a first demodulation scheme to said composite signal to generate at least a first demodulated signal; and
    means for automatically adjusting, using the one or more signal processors, the first demodulation scheme based at least in part on detector configuration data.

18. The system of claim 17, wherein the adjustment reduces crosstalk.

19. The system of claim 17, further comprising applying a second demodulation scheme to said composite signal to generate a second demodulated signal and adjusting the second demodulation scheme based at least in part on the second demodulated signal.

20. The system of claim 19, wherein said system further comprises means for adjusting, using the one or more processors, at least one of the first and second demodulation schemes in the absence of at least one of the first and second periodic pulses of electromagnetic energy.

* * * * *